US012751670B2

(12) United States Patent
Kim et al.

(10) Patent No.: US 12,751,670 B2
(45) Date of Patent: Oct. 6, 2026

(54) METHOD OF REMOVING EMI NOISE FROM PHOTOACOUSTIC SENSING SIGNAL AND PHOTOACOUSTIC SENSING APPARATUS EMPLOYING THE SAME

(71) Applicant: ELECTRONICS AND TELECOMMUNICATIONS RESEARCH INSTITUTE, Daejeon (KR)

(72) Inventors: Bong Kyu Kim, Daejeon (KR); Jong Deog Kim, Daejeon (KR)

(73) Assignee: ELECTRONICS AND TELECOMMUNICATIONS RESEARCH INSTITUTE, Daejeon (KR)

( * ) Notice: Subject to any disclaimer, the term of this patent is extended or adjusted under 35 U.S.C. 154(b) by 25 days.

(21) Appl. No.: 18/937,666

(22) Filed: Nov. 5, 2024

(65) Prior Publication Data

US 2025/0160759 A1 May 22, 2025

(30) Foreign Application Priority Data

Nov. 20, 2023 (KR) ........................ 10-2023-0160579
Sep. 13, 2024 (KR) ........................ 10-2024-0125373

(51) Int. Cl.
*A61B 5/00* (2006.01)
*A61B 5/145* (2006.01)

(52) U.S. Cl.
CPC .......... *A61B 5/7203* (2013.01); *A61B 5/0095* (2013.01); *A61B 5/14532* (2013.01)

(58) Field of Classification Search
CPC .. G01N 29/14; A61B 5/0095; A61B 5/14532; A61B 5/7203
See application file for complete search history.

(56) References Cited

U.S. PATENT DOCUMENTS

2015/0204822 A1* 7/2015 Horan ................ G01N 21/1702 73/643
2015/0297091 A1* 10/2015 Nakatsuka ......... G01N 29/2418 600/407

(Continued)

FOREIGN PATENT DOCUMENTS

JP 2007-64784 A 3/2007
JP 5429494 B2 2/2014

(Continued)

OTHER PUBLICATIONS

Y. Tanaka et al. "Resonant photo acoustic spectroscopy for a non invasive blood glucose monitoring human interface and temperature correction technology," Proceedings of SPIE, 2019, vol. 10878.

*Primary Examiner* — Gerald Johnson

(57) ABSTRACT

A photoacoustic sensing apparatus includes a light source that directs an optical signal toward an analyte, a photoacoustic sensor that receives an ultrasonic wave generated from the analyte and generates a photoacoustic sensor signal, and a signal processing device that controls the directing of the optical signal toward the analyte, and removes electromagnetic interference (EMI) noise from the photoacoustic sensor signal to generate a photoacoustic signal. A photoacoustic sensing method includes providing a first control signal to an optical switch connected to a light source to block or transmit the optical signal, generating a mixed signal that includes a photoacoustic signal and first EMI noise when the optical switch transmits the optical signal, and second EMI noise when the optical switch blocks the optical signal, and removing the EMI noise from the photoacoustic sensor signal based on the mixed signal and the second EMI noise.

16 Claims, 6 Drawing Sheets

(56) References Cited

U.S. PATENT DOCUMENTS

| | | | |
|---|---|---|---|
| 2017/0153206 A1 | 6/2017 | Sim et al. | |
| 2019/0064349 A1* | 2/2019 | Suzuki ................ | G01S 7/52077 |
| 2023/0138688 A1 | 5/2023 | Kim et al. | |

FOREIGN PATENT DOCUMENTS

| | | | |
|---|---|---|---|
| JP | 5584442 B2 | 9/2014 | |
| KR | 10-0281356 B1 | 2/2001 | |
| KR | 10-0871074 B1 | 11/2008 | |
| KR | 10-2020-0142102 A | 12/2020 | |
| KR | 10-2023-0063842 A | 5/2023 | |
| KR | 10-2023-0141063 A | 10/2023 | |

* cited by examiner

METHOD OF REMOVING EMI NOISE FROM PHOTOACOUSTIC SENSING SIGNAL AND PHOTOACOUSTIC SENSING APPARATUS EMPLOYING THE SAME

CROSS-REFERENCE TO RELATED APPLICATIONS

This application claims priority under 35 U.S.C. § 119 to Korean Patent Application Nos. 10-2023-0160579, filed on Nov. 20, 2023, and 10-2024-0125373, filed on Sep. 13, 2024, each of which is incorporated herein by reference in its entirety.

BACKGROUND

1. Technical Field

Embodiments of the present disclosure relates to a method of removing electromagnetic interference (EMI) noise from a photoacoustic sensing signal and a photoacoustic sensing apparatus employing the same.

2. Discussion of Related Art

The photoacoustic effect is a phenomenon in which, when a specific substance absorbs light and the temperature thereof increases, acoustic signals are generated because the thermal expansion transmits vibrations to the surrounding gas.

A photoacoustic sensing apparatus is an apparatus that measures changes in the content or composition ratio of a substance to be measured based on the photoacoustic effect.

For example, a photoacoustic sensing apparatus may measure gas concentration, measure biosignals noninvasively, or measure blood glucose levels noninvasively. Such optical sensing apparatuses extensively use high-sensitivity measurement technologies. However, in the case of noninvasive biosignal measuring sensors among the photo sensing apparatuses, the variations in the measurement signals are relatively small, leading to issues of measurement signals being distorted by subtle noise, such as electromagnetic interference (EMI).

SUMMARY

Embodiments of the present disclosure aims to provide an apparatus for removing electromagnetic interference (EMI) noise that is capable of compensating for EMI noise of an external device or a signal processing circuit to improve measurement accuracy of a photoacoustic signal, and a photoacoustic sensing apparatus employing the same.

Even weak EMI noise may cause distortion in measurement signals of a photoacoustic sensing apparatus. Therefore, it is difficult to secure measurement accuracy of a photoacoustic sensing apparatus. In particular, in the case of a noninvasive sensor, such as a noninvasive blood glucose meter, the measurement signal changes subtly with the variations in the amount of the substance to be measured. Therefore, EMI noise may have a significant effect on the measurement value of the sensor. Embodiments of the present disclosure aims to improve the measurement accuracy of a photoacoustic signal by measuring EMI noise and compensating for a measurement signal of a sensor based on the measurement result.

More specifically, embodiments of the present disclosure aims to provide a method of improving the measurement accuracy of a sensor system by extracting only an EMI noise component of a sensor system while the sensor system is in operation and compensating a photoacoustic measurement signal using the extracted component, and a photoacoustic sensing apparatus employing the same. EMI noise has various sources, such as a circuit for generating a light source signal of a sensor system, a signal processing circuit for detecting a reception signal, an external device, and the like. EMI noise emitted from such various sources may be detected by a reception circuit device of a photoacoustic sensing apparatus, and the photoacoustic sensing apparatus according to embodiments of the present disclosure detects such EMI noise and compensates a signal received from an analyte using the detected noise, enabling more accurate measurement of the physical quantity to be measured.

The technical objectives of embodiments of the present disclosure are not limited to the above, and other objectives that are not described above may become apparent to those of ordinary skill in the art based on the following descriptions.

According to an embodiment of the present disclosure, there is provided a photoacoustic sensing apparatus including: a light source that directs an optical signal toward an analyte; a photoacoustic sensor that receives an ultrasonic wave generated from the analyte and generates a photoacoustic sensor signal; and a signal processing device that controls the directing of the optical signal toward the analyte, and removes electromagnetic interference (EMI) noise from the photoacoustic sensor signal to generate a photoacoustic signal.

In an embodiment of the present disclosure, the signal processing device may generate a first clock signal and transmit the generated first clock signal to the light source, and the light source may modulate an intensity of the optical signal according to a specific frequency determined by the first clock signal.

In an embodiment of the present disclosure, the apparatus further comprises an optical switch that blocks or transmits the optical signal in response to a first control signal output from the signal processing device. The signal processing device generates a mixed signal including the photoacoustic signal and first EMI noise when the optical switch transmits the optical signal, and generates second EMI noise when the optical switch blocks the optical signal.

In an embodiment of the present disclosure, the signal processing device may classify the photoacoustic sensor signal into one of the mixed signal and the second EMI noise based on the first control signal, and analyzes the mixed signal and the second EMI noise to estimate information about the photoacoustic signal.

In an embodiment of the present disclosure, the signal processing device may include: a switch controller that generates the first control signal and a second control signal, and provides the first control signal to the optical switch to control the directing of the optical signal toward the analyte; an analog-to-digital converter (ADC) that converts the photoacoustic sensor signal into a digital signal; a selector that classifies the digital signal into one of the mixed signal and the second EMI noise based on the second control signal of the switch controller; and a processor that analyzes the mixed signal and the second EMI noise to estimate information about the photoacoustic signal.

In an embodiment of the present disclosure, the second control signal may be synchronized with the first control signal.

In an embodiment of the present disclosure, the ADC outputs the mixed signal when the first control signal sets the optical switch to an ON state. The ADC outputs the second EMI noise when the first control signal sets the optical switch to an OFF state.

In an embodiment of the present invention, the second EMI noise may be the digital signal when the first control signal is a control signal that sets the optical switch to an OFF state.

In an embodiment of the present disclosure, the signal processing device may further include a signal generator that may transmit a first clock signal to the light source such that the light source may modulate an intensity of the optical signal according to a specific frequency.

In an embodiment of the present disclosure, the signal processing device may further include a lock-in amplifier that may receive the photoacoustic sensor signal from the photoacoustic sensor, receive a second clock signal synchronized with the first clock signal from the signal generator, and detect a signal according to the specific frequency based on the second clock signal from the photoacoustic sensor signal. In this case, the ADC may convert the signal according to the specific frequency into the digital signal and provide the digital signal to the selector.

The information about the photoacoustic signal may include an amplitude and a phase or an x-component and a y-component amounts.

In an embodiment of the present disclosure, the processor may detect the mixed signal and the second EMI noise by dividing each of the mixed signal and the second EMI noise into an x-component and a y-component, and estimate the information about the photoacoustic signal based on a difference between the x-components of the mixed signal and the second EMI noise and a difference between the y-components of the mixed signal and the second EMI noise.

According to an embodiment of the present disclosure, there is provided a signal processing device for removing EMI noise in a photoacoustic sensor signal generated by a photoacoustic sensor based on an ultrasonic wave signal generated from an analyte to which an optical signal is directed.

The signal processing device may include: a switch controller that generates a first control signal and a second control signal, and provides the first control signal to an optical switch to control directing of the optical signal toward the analyte; an ADC that converts the photoacoustic sensor signal into a digital signal; a selector that classifies the digital signal into one of a mixed signal and second EMI noise based on the second control signal of the switch controller, the mixed signal including a photoacoustic signal and first EMI noise; and a processor that analyzes the mixed signal and the second EMI noise to estimate information of the photoacoustic signal.

In an embodiment of the present disclosure, the second control signal may be synchronized with the first control signal.

In an embodiment of the present disclosure, the ADC outputs the mixed signal when the first control signal may set the optical switch to an ON state.

In an embodiment of the present disclosure, the ADC outputs the second EMI noise when the first control signal may set the optical switch to an OFF state.

In an embodiment of the present disclosure, the signal processing device may further include a signal generator that may transmit a first clock signal to the light source such that the light source may modulate an intensity of the optical signal according to a specific frequency.

In an embodiment of the present disclosure, the signal processing device may further include a lock-in amplifier that may receive the photoacoustic sensor signal from the photoacoustic sensor, receive a second clock signal synchronized with the first clock signal from the signal generator, and detect a signal according to the specific frequency based on the second clock signal from the photoacoustic sensor signal. In this case, the ADC may convert the signal according to the specific frequency into the digital signal, and provide the digital signal to the selector.

In an embodiment of the present disclosure, the processor may detect the mixed signal and the second EMI noise by dividing each of the mixed signal and the second EMI noise into an x-component and a y-component, and estimate the information of the photoacoustic signal based on a difference between the x-components of the mixed signal and the second EMI noise and a difference between the y-components of the mixed signal and the second EMI noise.

According to an embodiment of the present disclosure, there is provided a photoacoustic sensing method for removing EMI noise in a photoacoustic sensor signal generated by a photoacoustic sensor based on an ultrasonic wave signal generated from an analyte to which an optical signal is directed.

The photoacoustic sensing method may include: providing a first control signal to an optical switch connected to a light source to block or transmit the optical signal; generating a mixed signal that includes a photoacoustic signal and first EMI noise when the optical switch transmits the optical signal, and second EMI noise when the optical switch blocks the optical signal; and removing the EMI noise from the photoacoustic sensor signal based on the mixed signal and the second EMI noise to generate a photoacoustic signal. Generating the mixed signal and the second EMI noise includes converting the photoacoustic sensor signal into a first digital signal; receiving a second control signal synchronized with the first control signal and classifying the first digital signal into one of the mixed signal and the second EMI noise based on the second control signal, and transmitting the second EMI noise to a processor; providing a first clock signal to the light source to control the light source to modulate an intensity of the optical signal according to a specific frequency, and a second clock signal synchronized with the first clock signal to a lock-in amplifier; receiving, by the lock-in amplifier, the photoacoustic sensor signal from the photoacoustic sensor, and detecting a signal according to the specific frequency based on the second clock signal from the photoacoustic sensor signal; and converting the signal detected by the lock-in amplifier into the first digital signal.

In an embodiment of the present disclosure, the method further includes analyzing the mixed signal and the second EMI noise to estimate information about the photoacoustic signal. Analyzing the mixed signal and the second EMI noise includes: analyzing the second EMI noise to derive an x-component and a y-component of the second EMI noise; analyzing the mixed signal to derive an x-component and a y-component of the mixed signal; and estimating the information of the photoacoustic signal based on the x-component and the y-component of the second EMI noise and the x-component and the y-component of the mixed signal.

BRIEF DESCRIPTION OF THE DRAWINGS

The above and other objects, features and advantages of various embodiments of the present disclosure will become more apparent to those of ordinary skill in the art by describing some embodiments thereof in detail with reference to the accompanying drawings, in which.

DETAILED DESCRIPTION OF EMBODIMENTS

Figure 1:
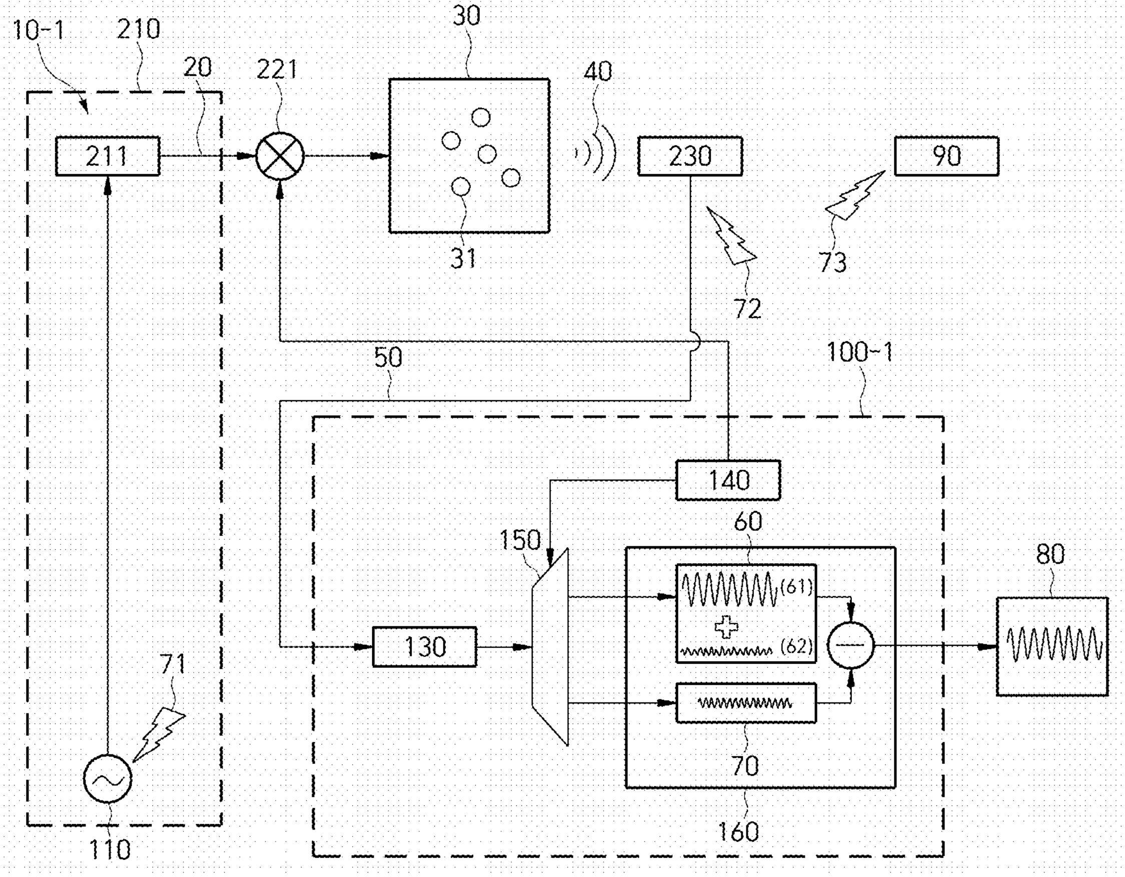
FIG. 1 is a block diagram showing a configuration of a photoacoustic sensing apparatus according to a first embodiment of the present disclosure.

Hereinafter, the advantages and features of various embodiments of the present disclosure and ways of achieving them will become readily apparent with reference to the detailed description of the following embodiments in conjunction with the accompanying drawings. However, embodiments of the present disclosure are not limited to such embodiments and may be embodied in various forms.

Terms used herein are used to aid in the description and understanding of the embodiments and are not intended to limit the scope and embodiments of the present disclosure. It should be understood that the singular forms "a" and "an" also include the plural forms unless the context clearly dictates otherwise. The terms "comprise," "comprising," "include," and/or "including" used herein specify the presence of stated features, integers, steps, operations, elements, components and/or groups thereof and do not preclude the presence or addition of one or more other features, integers, steps, operations, elements, components, and/or groups thereof.

It should be understood that, although the terms "first," "second," etc. may be used herein to describe various elements, these elements are not limited by these terms. These terms are only used for distinguishing one element from another. For example, a first element could be called a second element, and vice versa It will be understood that when a first element is referred to as being "connected" or "coupled" to a second element, the first element can be directly connected or coupled to the second element or intervening elements may be present therebetween. In contrast, when an element is referred to as being "directly connected" or "directly coupled" to another element, there are no intervening elements present therebetween. Other words used to describe the relationship between elements should be interpreted in a like fashion (i.e., "between" versus "directly between," "adjacent" versus "directly adjacent," etc.).

In the description of embodiments of the present disclosure, when it is determined that a detailed description of related technology may unnecessarily obscure the gist of these embodiments, the detailed description may be omitted for the interest of brevity.

Hereinafter, some embodiments of the present disclosure will be described with reference to the accompanying drawings in detail. For better understanding of the present disclosure, the same reference numerals are used to refer to the same elements through the description of the figures.

FIG. 1 is a block diagram showing a configuration of a photoacoustic sensing apparatus according to a first embodiment of the present disclosure.

A photoacoustic sensing apparatus 10-1 is an apparatus for directing an optical signal 20 to an analyte 31, detecting ultrasonic waves 40 generated from the analyte 31 through a photoacoustic sensor 230 to generate a photoacoustic sensor signal 50, and extracting a photoacoustic signal 80 based on the photoacoustic sensor signal 50.

The photoacoustic sensing apparatus 10-1 may be affected by various types of EMI noise. Therefore, the photoacoustic sensing apparatus 10-1 may detect not only a photoacoustic signal that is a detection target, but also a mixed signal 60 that is a combination of a photoacoustic signal and EMI noise.

In this specification, EMI noise included in the mixed signal 60 is referred to as first EMI noise 62, and EMI noise detected alone, excluding the photoacoustic signal 61, is referred to as second EMI noise 70.

EMI noise has various sources. For example, there may be EMI noise 71 generated from a signal generator 110 for driving an optical element 211, EMI noise 72 generated from the photoacoustic sensor 230, EMI noise 73 generated in the environment of the photoacoustic sensing apparatus 10-1, such as an external device 90, and the like.

Therefore, the photoacoustic sensor signal 50 output by the photoacoustic sensor 230 is usually a mixed signal 60 in which the photoacoustic signal 61 and the first EMI noise 62 are mixed, and may be a distorted measurement signal.

Figure 2:
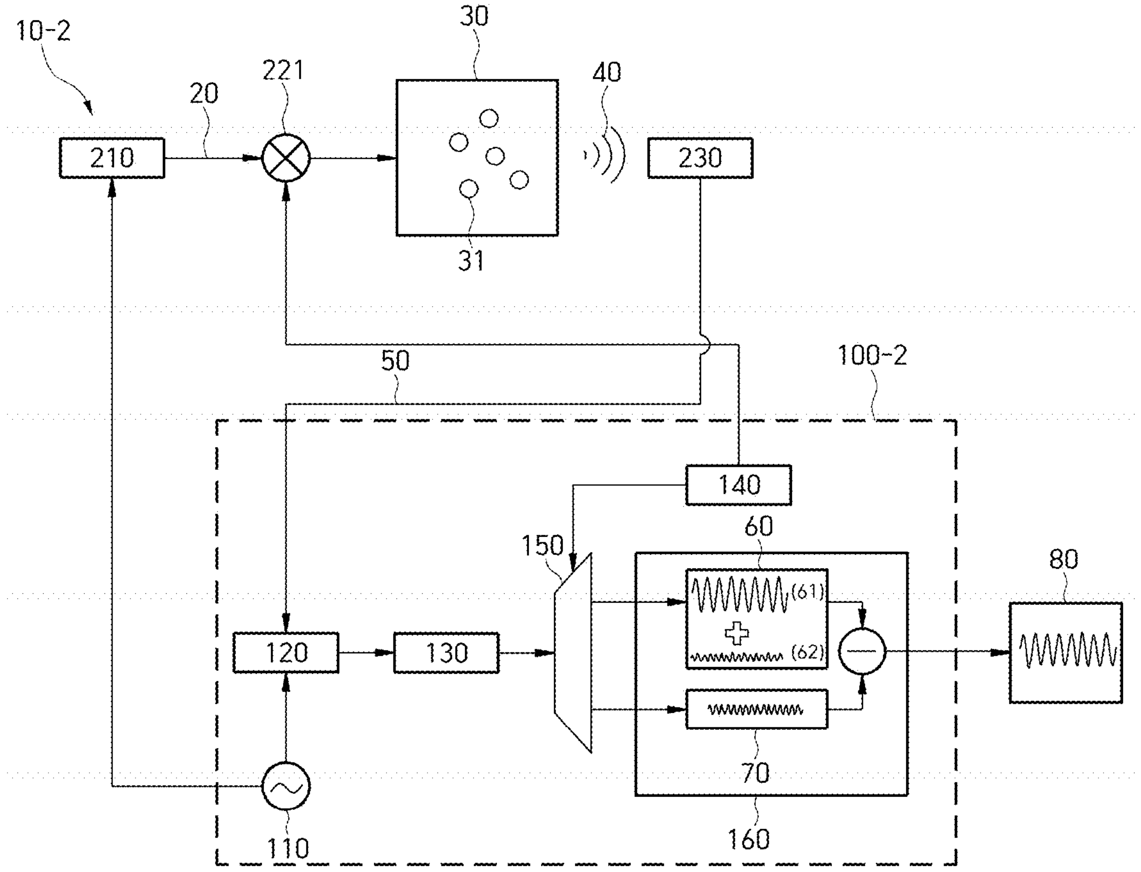
FIG. 2 is a block diagram showing a configuration of a photoacoustic sensing apparatus according to a second embodiment of the present disclosure.
Figure 3:
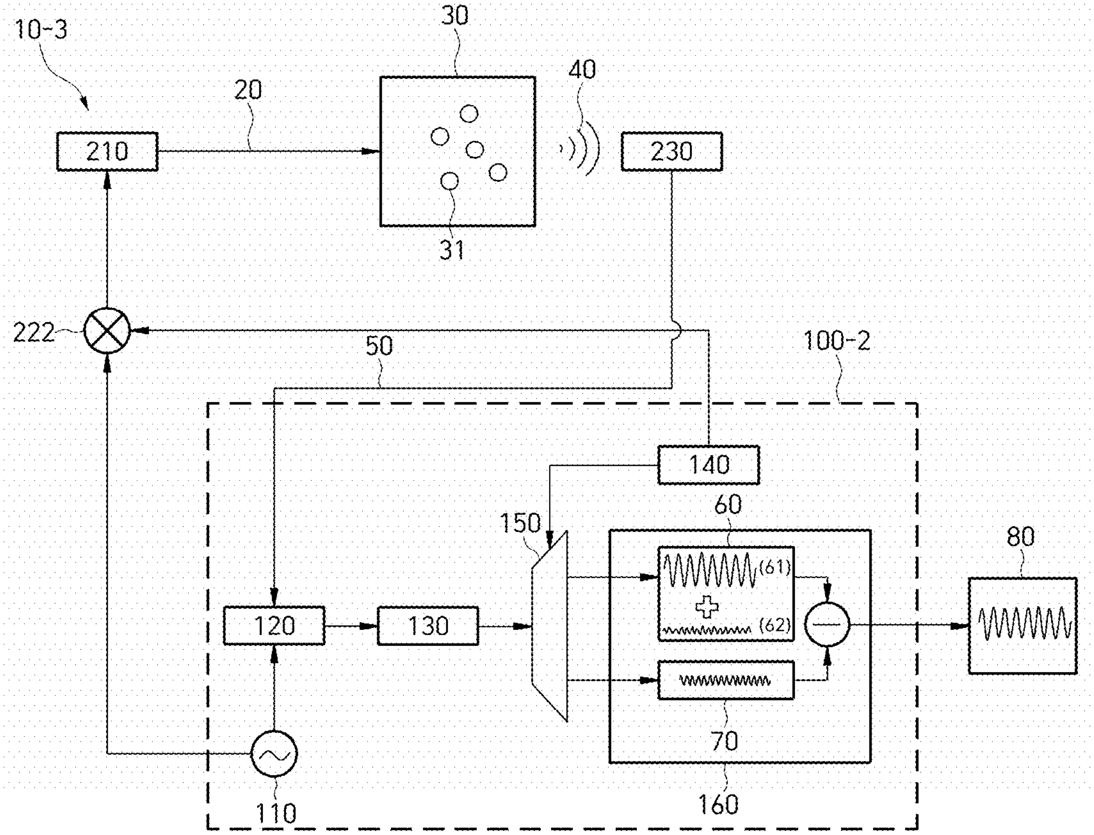
FIG. 3 is a block diagram showing a configuration of a photoacoustic sensing apparatus according to a third embodiment of the present disclosure.

Details described above regarding the occurrence and influence of EMI noise also apply to a photoacoustic sensing apparatus 10-2 shown in FIG. 2 or a photoacoustic sensing apparatus 10-3 shown in FIG. 3.

The photoacoustic sensing apparatus 10-1 according to an embodiment of the present disclosure may operate in the order of the following operations S1 to S3.

First, the photoacoustic sensing apparatus 10-1 measures second EMI noise 70 (S1). Then, the photoacoustic sensing apparatus 10-1 measures a mixed signal 60 of a photoacoustic signal 61 and first EMI noise 62 (S2). Then, the photoacoustic sensing apparatus 10-1 subtracts the second EMI noise 70 from the mixed signal 60, thereby generating an undistorted photoacoustic signal 80 with minimized influence of EMI noise (S3). In operation S1, the photoacoustic sensing apparatus 10-1 blocks the optical signal 20 directed to a light absorber 30 while operating all components included in the photoacoustic sensing apparatus 10-1 to obtain the second EMI noise 70. The second EMI noise 70 is a measurement signal that combines EMI noise 71 generated from a light source 210, EMI noise 72 generated from a photoacoustic sensor 230, and EMI noise 73 generated in the environment including an external device 90.

Referring to FIG. 1, the photoacoustic sensing apparatus 10-1 according to an embodiment of the present disclosure includes a signal processing device 100-1, a light source 210, an optical switch 221, and a photoacoustic sensor 230. The signal processing device 100-1 according to an embodiment of the present disclosure includes an analog-to-digital converter (ADC) 130, a switch controller 140, a selector 150, and a processor 160. In some embodiments, the signal processing device 100-1 may further include a signal generator 110.

The photoacoustic sensing apparatus 10-1 and the signal processing device 100-1 illustrated in FIG. 1 are provided, and the components of the photoacoustic sensing apparatus 10-1 and the signal processing device 100-1 according to embodiments of the present disclosure are not limited to the embodiment shown in FIG. 1, and some components may be added, changed, or omitted as needed.

The light source 210 generates an optical signal 20, and provides the optical signal 20 to the light absorber 30 when the optical switch 221 is in an ON state. The light absorber 30 may include an analyte 31, and in this case, the analyte 31 generates ultrasonic waves 40.

In the embodiment of FIG. 1, the light source 210 may include a signal generator 110 that drives an optical element 211 and the optical element 211 that generates an optical signal 20. In some embodiments, the signal generator 110 may be separated from the light source 210 and included in the signal processing device 100-1.

The optical element 211 is an element that generates light. For example, the optical element 211 may be a laser, a laser diode (LD), or a light-emitting diode (LED). The signal generator 110 adjusts the intensity of the optical signal 20 generated from the optical element 211 using a current signal or a voltage signal.

The waveform of the optical signal 20 output from the light source 210 is determined according to an output signal of the signal generator 110. When the optical switch 221 is turned on (closed), the optical signal 20 output from the light source 210 reaches the light absorber 30, and the analyte 31 included in the light absorber 30 generates ultrasonic waves 40 due to the influence of the optical signal 20.

The optical switch 221 is an element that blocks or transmits the optical signal 20 and is controlled by the switch controller 140 of the signal processing device 100-1. The optical switch 221, when turned on (closed), allows the optical signal 20 to be transmitted to the light absorber 30, and when turned off (open), blocks the optical signal 20 from being transmitted to the light absorber 30.

By measuring the changes in the size and phase of the ultrasonic waves 40, the type, concentration, and amount of the analyte 31 included in the light absorber 30 may be analyzed. For example, the light absorber 30 may be skin tissue of a human body, and the analyte 31 may be glucose that constitutes blood sugar. However, the light absorber 30 and the analyte 31 are not limited to the above-described examples, and may vary according to embodiments of the present disclosure.

The photoacoustic sensor 230 receives ultrasonic waves 40 generated from the analyte 31 to generate a photoacoustic sensor signal 50, which is an electrical signal, and provides the photoacoustic sensor signal 50 to the ADC 130 included in the signal processing device 100-1. The ADC 130 converts the photoacoustic sensor signal 50 into a digital signal and provides the digital signal to the selector 150.

The photoacoustic sensor 230 may include an ultrasonic element that converts the received ultrasonic waves 40 into an electrical signal, and a signal amplifier that amplifies the converted electrical signal. That is, the photoacoustic sensor 230 may convert ultrasonic waves 40 generated from the analyte 31 into electric signals and amplify the electric signals. For example, the ultrasonic element may include a piezoelectric sensor. However, embodiments of the present disclosure are not limited to the configuration of the ultrasonic element described above.

As described above, the photoacoustic sensing apparatus 10-1 generates first and second EMI noise 62 and 70 and is affected by the first and second EMI noise 62 and 70. Therefore, the photoacoustic sensor signal 50 output by the photoacoustic sensor 230 may be a mixed signal 60 of a photoacoustic signal 61 derived from the analyte 31 and first EMI noise 62.

The first EMI noise 62 or the second EMI noise 70 may include at least one of EMI noise 71 from the signal generator 110, EMI noise from the light source 210, or EMI noise 72 generated by the photoacoustic sensor 230. As used herein, including in the claims, "or" as used in a list of items prefaced by a phrase such as "at least one of" or "one or more of" or "one or both of" indicates an inclusive list such that, for example, a list of at least one of A, B, or C indicates A or B or C or AB or AC or BC or ABC (i.e., A and B and C). For example, the EMI noise 72 may be generated by a signal processing board included in the photoacoustic sensor 230, which includes an ultrasonic element (or an electric signal converter), a signal amplifier, and a power supply. In addition, the EMI noise 73 generated in the environment of the photoacoustic sensing apparatus 10-1, such as an external device 90, may also affect the photoacoustic sensor signal 50.

Hereinafter, an EMI noise compensation mechanism of the photoacoustic sensing apparatus 10-1 will be described. In an embodiment, the signal processing device 100-1 controls directing of the optical signal 20 toward the analyte 31 and removes EMI noise from the photoacoustic sensor signal 50 to generate the photoacoustic signal 80.

The signal processing device 100-1 blocks the optical switch 221 through the switch controller 140 such that the optical signal 20 emitted from the light source 210 is not transmitted to the light absorber 30, thereby measuring the second EMI noise 70. That is, the optical switch 221 has a function of transmitting or blocking the optical signal 20 to the light absorber 30 under the control of the switch controller 140.

The switch controller 140 may generate a first control signal and provide the first control signal indicative of a first state (e.g., an OFF state) to the optical switch 221 such that the optical switch 221 does not transmit the optical signal 20 to the light absorber 30, and in this case, the photoacoustic sensor signal 50 output from the photoacoustic sensor 230 corresponds to the second EMI noise 70. For example, the ADC 130 outputs the second EMI noise 70 as a digital signal when the first control signal sets the optical switch 221 to an OFF state.

In addition, the switch controller 140 may transmit the first control signal indicative of a second state (e.g., an ON state) to the optical switch 221 such that the optical switch 221 transmits the optical signal 20 to the light absorber 30, and in this case, the photoacoustic sensor signal 50 output from the photoacoustic sensor 230 corresponds to a mixed signal 60 of the photoacoustic signal 61 and the first EMI noise 62. For example, the ADC 130 outputs the mixed signal 60 as a digital signal when the first control signal sets the optical switch 221 to an ON state.

The selector 150 receives the photoacoustic sensor signal 50 from the photoacoustic sensor 230, classifies the photoacoustic sensor signal 50 into the mixed signal 60 or the second EMI noise 70 based on a second control signal of the switch controller 140, and transmits the classified photoacoustic sensor signal 50 to the processor 160. For example, the selector 150 receives a digital signal corresponding to the photoacoustic sensor signal 50, and classifies the digital signal into one of the mixed signal and the second EMI noise 70 based on a second control signal of the switch controller 140.

The selector 150 may, when synchronized with the optical switch 221, separate photoacoustic sensor signals 50 into a mixed signal 60 and second EMI noise 70. That is, when a control signal transmitted from the switch controller 140 to the optical switch 221 is referred to as a "first control signal" and a control signal transmitted from the switch controller 140 to the selector 150 is referred to as a "second control signal," the switch controller 140 may synchronize the first control signal and the second control signal such that the selector 150 may classify the photoacoustic sensor signal 50 into one of a mixed signal 60 and second EMI noise 70. For example, the switch controller 140 may synchronize the first control signal that opens (off) the optical switch 221 with the second control signal that allows the selector 150 to classify the photoacoustic sensor signal 50 as the second EMI noise 70, thereby allowing the photoacoustic sensor signal 50 to be classified as the second EMI noise 70. In addition, the switch controller 140 may synchronize the first control signal that closes (on) the optical switch 221 with the second control signal that allows the selector 150 to classify the photoacoustic sensor signal 50 as the mixed signal 60, thereby allowing the photoacoustic sensor signal 50 to be classified as the mixed signal 60.

For example, the selector 150 may be a demultiplexer (DeMUX). In addition, for example, the selector 150 may be controlled by a software program. However, embodiments of the present disclosure are not limited to the configuration and control method of the selector 150.

The selector 150 transmits the classified signal to the processor 160, and the processor 160 may remove the second EMI noise 70 from the mixed signal 60, thereby generating the photoacoustic signal 80. That is, the processor 160 generates the photoacoustic signal 80 through a differential operation of the mixed signal 60 and the second EMI noise 70. The processor 160 may be a digital signal processor. The smaller the difference between the points in time of measuring the mixed signal 60 and the second EMI noise 70, the more similar the first EMI noise 62 and the second EMI noise 70 may be. In this way, the signal processing device 100-1 may extract the photoacoustic signal 80 derived from the analyte 31 while minimizing the influence of the first EMI noise 62. That is, the photoacoustic signal 80 generated by the processor 160 is a signal substantially without the first EMI noise 62 or with significantly reduced influence of the first EMI noise 62.

FIG. 2 is a block diagram showing a configuration of a photoacoustic sensing apparatus according to a second embodiment of the present disclosure. A photoacoustic sensing apparatus 10-2 illustrated in FIG. 2 is an example of a photoacoustic sensing apparatus implemented using a lock-in amplifier (LIA).

Referring to FIG. 2, the photoacoustic sensing apparatus 10-2 according to an embodiment of the present disclosure includes a signal processing device 100-2, a light source 210, an optical switch 221, and a photoacoustic sensor 230. The signal processing device 100-2 according to an embodiment of the present disclosure includes a signal generator 110, a lock-in amplifier 120, an ADC 130, a switch controller 140, a selector 150, and a processor 160.

The photoacoustic sensing apparatus 10-2 also uses a method in which the signal generator 110 modulates an optical signal 20 emitted from a light source 210, similar to the photoacoustic sensing apparatus 10-1. The photoacoustic sensing apparatus 10-2 is equipped with a lock-in amplification technology, thus having a benefit of precisely detecting a microscopic signal.

The signal generator 110 transmits a first clock signal to the light source 210 such that the light source 210 modulates the optical output intensity of the optical signal 20 according to a specific frequency. That is, the optical signal 20 emitted from the light source 210 may have a varying intensity or may alternate between being turned on and off according to a specific frequency provided by the signal generator 110.

In addition, the signal generator 110 inputs a second clock signal synchronized with the first clock signal to the lock-in amplifier 120, and the lock-in amplifier 120 selectively detects only a signal of a specific frequency component from the photoacoustic sensor signal 50 using the second clock signal. The ADC 130 converts the signal detected by the lock-in amplifier 120 into a digital signal and transmits the digital signal to the selector 150.

In an embodiment of the present disclosure, the lock-in amplifier 120 may output x-components and y-components of the mixed signal 60 and the second EMI noise 70, or output the amplitudes and the phases of the mixed signal 60 and the second EMI noise 70. In this case, the processor 160 may calculate the amplitude and the phase of the photoacoustic signal 80 based on the x-component and y-component of the mixed signal 60 and the second EMI noise 70, and may calculate the amplitude and the phase of the photoacoustic signal 80 based on the amplitudes and the phases of the mixed signal 60 and the second EMI noise 70.

Similar to the embodiment of FIG. 1, the switch controller 140 provides a first control signal to the optical switch 221 to control the optical switch 221, and provides a second control signal to the selector 150 to control the selector 150. The switch controller 140 may synchronize the first control signal and the second control signal to allow the selector 150 to classify the digital signal received from the ADC 130 into one of the mixed signal 60 and the second EMI noise 70.

The processor 160 classifies an output signal of the ADC 130 as the second EMI noise 70 when the switch controller 140 controls the optical switch 221 to be in an OFF state, and classifies an output signal of the ADC 130 as the mixed signal 60 when the switch controller 140 controls the optical switch 221 to be in an ON state. The processor 160 calculates the difference between the mixed signal 60 and the second EMI noise 70 to detect the photoacoustic signal 80.

FIG. 3 is a block diagram showing a configuration of a photoacoustic sensing apparatus according to a third embodiment of the present disclosure.

Similar to the second embodiment, the third embodiment is an example of a photoacoustic sensing apparatus implemented using a lock-in amplifier, and differs from the second embodiment in that an switch (e.g., electrical switch) 222 is disposed between a signal generator 110 and a light source 210. The electrical switch 222 transmits or blocks an output signal of the signal generator 110 in the signal processing device 100-2 to the light source 210, in response to a first control signal output from the signal processing device 100-2. The switch controller 140 controls the opening and closing of the electrical switch 222. The photoacoustic sensing apparatus 10-3 may apply or block an optical signal 20 to the light absorber 30 through the mechanism. That is, the light source 210 generates an optical signal 20 based on a first clock signal input from the signal generator 110 according to the switching control of the electrical switch 222, and the generated optical signal 20 is applied to the light absorber 30.

The method of measuring and compensating for EMI noise of the photoacoustic sensing apparatus 10-3 is substantially the same as that of the second embodiment, and thus the detailed descriptions thereof have been omitted in the interest of brevity.

FIG. 4 is a diagram for describing a method of obtaining components of a photoacoustic signal based on a mixed signal and EMI noise. In FIG. 4, an example of obtaining the difference between a mixed signal 60 and second EMI noise 70 is illustrated. The technical details of FIG. 4 may be performed by the photoacoustic sensing apparatus 10-1, the photoacoustic sensing apparatus 10-2, and the photoacoustic sensing apparatus 10-3.

The mixed signal 60 is a signal in which a photoacoustic signal 61 and first EMI noise 62 are mixed. Even when the magnitudes of the photoacoustic signal 61 and the first EMI noise 62 are the same at different measurement points in time (T1 and T2), when the phases of the photoacoustic signal 61 and the first EMI noise 62 are different, the magnitude and the phase of the mixed signal 60 may change. Since embodiments of the present disclosure estimate the first EMI noise 62 as the second EMI noise 70, the effect of the phase needs to be considered when obtaining the components of the photoacoustic signal 80 by obtaining the difference between the mixed signal 60 and the second EMI noise 70.

Figure 4A:
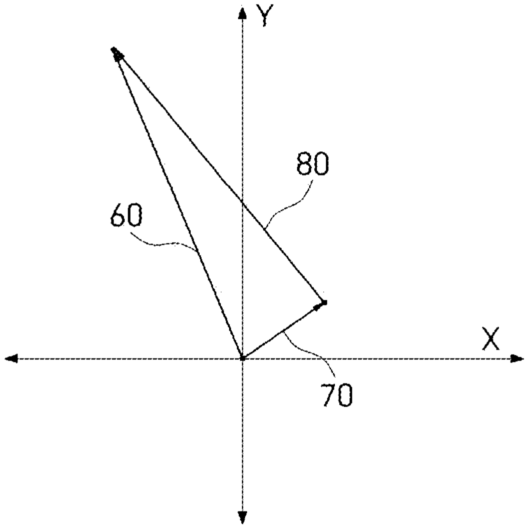
FIGS. 4A and 4B are diagrams for describing a method of obtaining components of a photoacoustic signal based on a mixed signal and EMI noise.
Figure 4B:
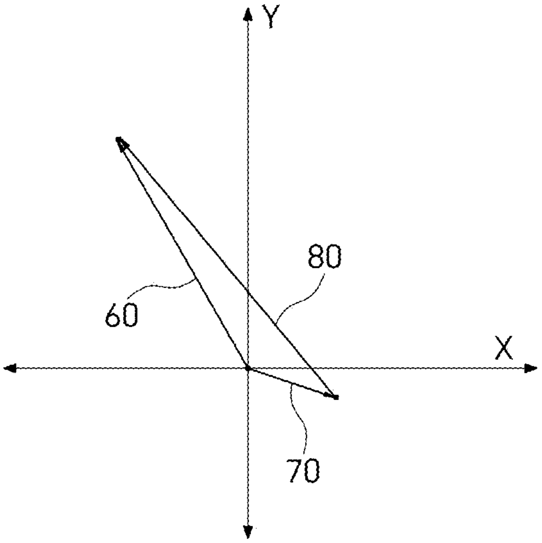

As shown in FIG. 4A, when the phase difference between the photoacoustic signal 80 and the second EMI noise 70 is 90 degrees or less, the mixed signal 60 may be measured larger than the photoacoustic signal 80, and as shown in FIG. 4B, when the phase difference between the photoacoustic signal 80 and the second EMI noise 70 is 90 degrees or more, the mixed signal 60 may be measured smaller than the photoacoustic signal 80. Here, it is assumed that the size of the second EMI noise 70 is sufficiently small compared to the size of the photoacoustic signal 80.

By measuring the signal size (or amplitude) and the phase of the mixed signal 60 and the second EMI noise 70 to extract the photoacoustic signal 80, or by separately measuring the x-components and the y-components of the mixed signal 60 and the second EMI noise 70 to extract the photoacoustic signal 80, the photoacoustic signal 80 with a minimized influence of EMI noise may be more accurately estimated.

In the second and third embodiments, the processor 160 may detect the sizes and the phases of the mixed signal 60 and the second EMI noise 70, or the x-components and the y-components of the mixed signal 60 and the second EMI noise 70, based on a signal generated by the lock-in amplifier 120.

The processor 160 may detect the mixed signal 60 and the signal of the second EMI noise 70 output by the lock-in amplifier 120 and converted into a digital signal by the ADC 130 by separating the mixed signal 60 and the signal of the second EMI noise 70 into x-components and y-components, and may accurately generate the photoacoustic signal 80, in which EMI noise is compensated for without signal distortion, by calculating the difference in the magnitude of each component. As another example, the processor 160 may also generate the photoacoustic signal 80 by measuring the amplitudes and the phases of the mixed signal 60 and the second EMI noise 70 and compensating for the EMI noise.

Figure 5A:
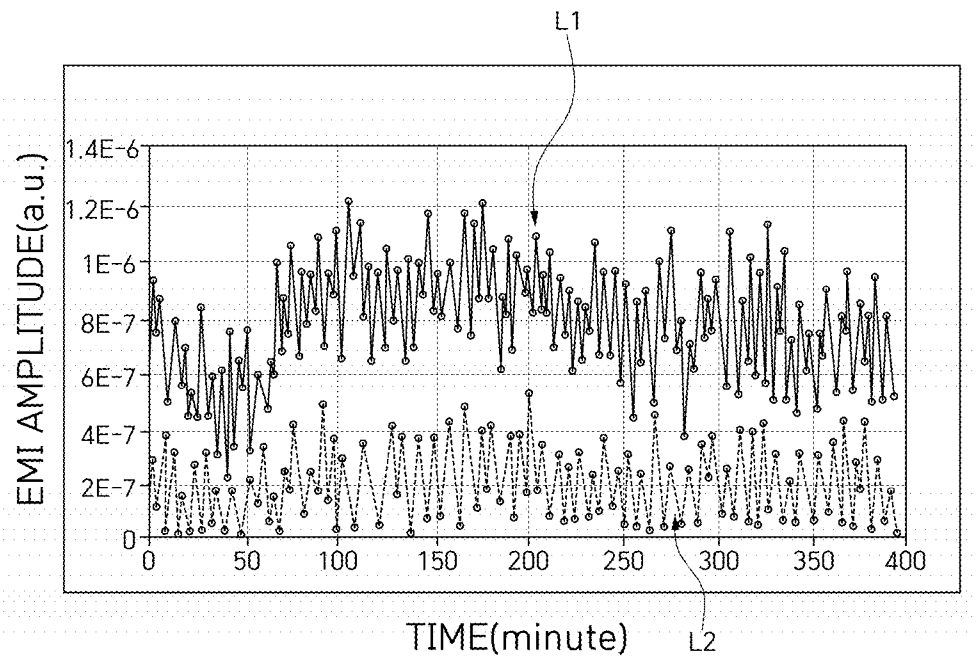
FIGS. 5A and 5B are graphs showing the results of measuring EMI noise and FIG. 6 is a flowchart for describing a photoacoustic sensing method according to an embodiment of the present disclosure.
Figure 5B:
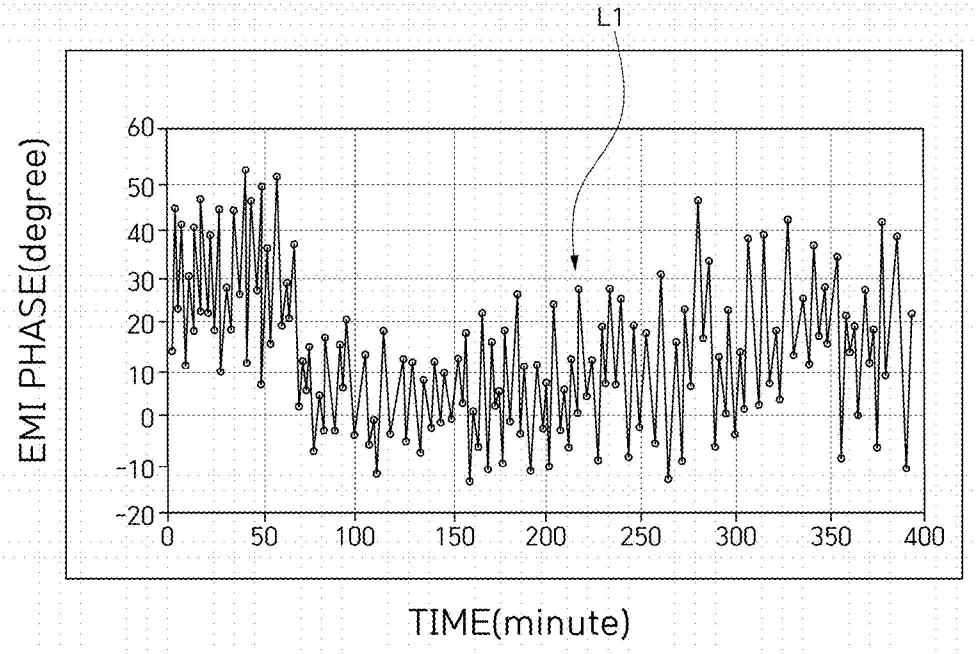

FIGS. 5A and 5B are graphs showing the results of measuring EMI noise.

The amplitude of the EMI noise may vary depending on the type of the light source L1 or L2 (see FIG. 5A). The amplitude (see FIG. 5A) and the phase (see FIG. 5B) of EMI noise change over time. Therefore, in order to precisely measure the photoacoustic signal 80, it is required to measure the second EMI noise 70 at a relatively short cycle.

Embodiments of the present disclosure have a benefit of improving the measurement accuracy and precision of the photoacoustic signal by reducing signal distortion due to EMI noise.

Figure 6:
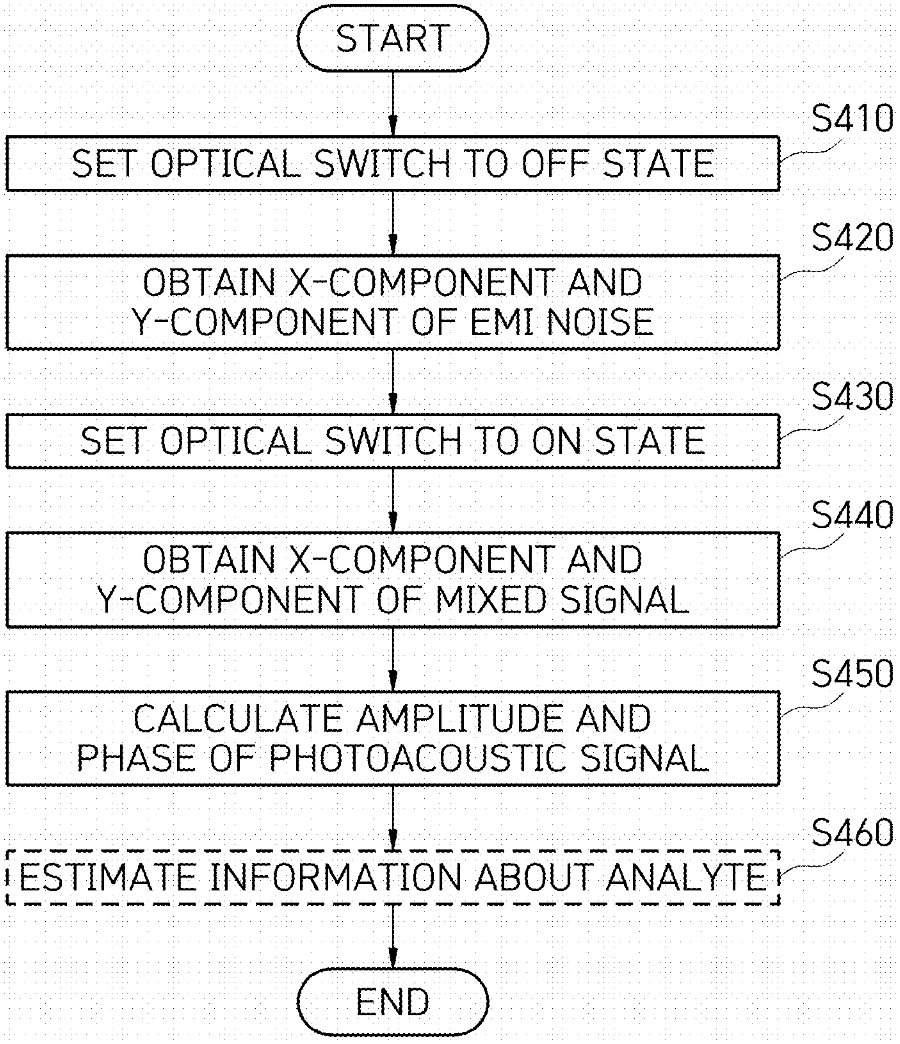

FIG. 6 is a flowchart for describing a photoacoustic sensing method according to an embodiment of the present disclosure. The photoacoustic sensing method is a method of removing EMI noise from a photoacoustic sensor signal. In other words, the photoacoustic sensing method is a data processing method of estimating a photoacoustic signal generated from an analyte by compensating for EMI noise.

Referring to FIG. 6, the photoacoustic sensing method according to an embodiment of the present disclosure includes operations S410 to S460. Operations of the photoacoustic sensing method according to embodiments of the present disclosure are not limited to the embodiment illustrated in FIG. 6, and some operations may be added, changed, or omitted as needed.

For convenience of description, it is assumed that the photoacoustic sensing method illustrated in FIG. 6 is performed by the photoacoustic sensing apparatus 10-2 in FIG. 2.

Operation S410 is an operation of setting the optical switch to an OFF state.

The switch controller 140 transmits a first control signal to the optical switch 221 connected to the light source 210 to set the optical switch 221 to an OFF state. Therefore, the optical signal 20 emitted from the light source 210 is blocked, and the optical signal 20 is not directed toward the analyte 31.

Meanwhile, the switch controller 140 transmits a second control signal (off) to the selector 150 at the same time at which the switch controller 140 transmits the first control signal (off) to the optical switch 221.

Operation S420 is an operation of obtaining an x-component and a y-component of EMI noise.

Since the optical switch 221 is set to the OFF state, the photoacoustic sensor signal 50 generated by the photoacoustic sensor 230 corresponds to second EMI noise 70.

The lock-in amplifier 120 receives the photoacoustic sensor signal 50 from the photoacoustic sensor 230 and receives a second clock signal synchronized with the first clock signal from the signal generator 110. The lock-in amplifier 120 detects a signal according to the specific frequency that has been applied to the intensity modulation of the optical signal 20 from the photoacoustic sensor signal 50 based on the second clock signal.

The ADC 130 converts the signal detected by the lock-in amplifier 120 into a digital signal and transmits the digital signal to the selector 150, and the selector 150 classifies the digital signal as second EMI noise 70 based on the second control signal of the switch controller 140 and transmits the second EMI noise to the processor 160. In other words, the selector 150 may output the digital signal corresponding to the second EMI noise 70 based on the second control signal indicating a first state. For example, the second control signal (e.g., indicating an "OFF" state") is a signal synchronized with the first control signal.

The processor 160 may analyze the second EMI noise 70 to derive an x-component Nx and a y-component Ny of the second EMI noise 70.

Operation S430 is an operation of setting the optical switch to the ON state.

The signal generator 110 transmits a first clock signal to the light source 210 such that the light source 210 modulates the intensity of the optical signal 20 according to a specific frequency.

The switch controller 140 transmits a first control signal to the optical switch 221 connected to the light source 210 to set the optical switch 221 to an ON state. Accordingly, the optical signal 20 emitted from the light source 210 is directed toward the analyte 31. The switch controller 140 transmits a second control signal (on) to the selector 150 at the same time at which it transmits the first control signal (on) to the optical switch 221.

Operation S440 is an operation of obtaining an x-component and a y-component of a mixed signal.

Since the optical switch 221 is set to the ON state, the photoacoustic sensor signal 50 generated by the photoacoustic sensor 230 corresponds to a mixed signal 60.

The lock-in amplifier 120 receives the photoacoustic sensor signal 50 from the photoacoustic sensor 230 and receives a second clock signal synchronized with the first clock signal from the signal generator 110. The lock-in amplifier 120 detects a signal according to the specific frequency that has been applied to the intensity modulation of the optical signal 20 from the photoacoustic sensor signal 50 based on the second clock signal.

The ADC 130 converts the signal detected by the lock-in amplifier 120 into a digital signal and transmits the digital signal to the selector 150, and the selector 150 classifies the digital signal as a mixed signal 60 based on the second control signal of the switch controller 140 and transmits the mixed signal to the processor 160. In other words, the selector 150 may output the digital signal corresponding to the mixed signal 60 based on the second control signal indicating a second state. For example, the second control signal (e.g., indicating an "ON" state) is a signal synchronized with the first control signal.

The processor 160 may analyze the mixed signal 60 to derive an x-component Rx and a y-component Ry of the mixed signal 60.

Operation S450 is an operation of calculating the amplitude and the phase of a photoacoustic signal.

The processor 160 estimates a photoacoustic signal 80 based on the mixed signal 60 and the second EMI noise 70.

The processor 160 may calculate an x-component Rx-Nx and a y-component Ry-Ny of the photoacoustic signal 80 based on the x-component Rx and the y-component Ry of the mixed signal 60 and the x-component Nx and the y-component Ny of the second EMI noise 70, and may calculate the amplitude and the phase of the photoacoustic signal 80 using the x-component Rx-Nx and the y-component Ry-Ny of the photoacoustic signal 80. Specifically, the processor 160 may calculate a difference Rx-Nx between the x-component Rx of the mixed signal 60 and the x-component Nx of the second EMI noise 70 and a difference Ry-Ny between the y-component Ry of the mixed signal 60 and the y-component Ny of the second EMI noise 70, thereby calculating the amplitude and the phase of the photoacoustic signal 80 using the differences Rx-Nx and Ry-Ny to estimate information about the photoacoustic signal 80.

Operation S460 is an operation of estimating information about the analyte.

The processor 160 may estimate information, such as the type, amount, and concentration of the analyte 31, based on the amplitude and the phase of the photoacoustic signal 80 using a table, a formula, or a model that is previously stored.

The photoacoustic sensing method has been described above with reference to the flowcharts presented in the drawings. While the above method has been shown and described as a series of blocks for the purpose of simplicity, it is to be understood that embodiments of the present disclosure are not limited to the order of the blocks, and that some blocks may be executed in a different order from that shown and described herein or executed concurrently with other blocks, and various other branches, flow paths, and sequences of blocks that achieve the same or similar results may be implemented. In addition, not all illustrated blocks may be required for implementation of the method described herein.

Meanwhile, in the description with reference to FIG. 6, each operation may be further divided into a larger number of sub-operations or combined into a smaller number of operations according to examples of implementation of the present invention. In addition, some of the operations may not be performed or the order of operations may be changed as needed. In addition, even in the case of omitted content, the content of FIG. 1 to FIG. 5 (FIGS. 5A and 5B) may be applied to the content of FIG. 6. In addition, the content of FIG. 6 may be applied to the content of FIGS. 1 to 5 (FIGS. 5A and 5B).

In an embodiment, a photoacoustic sensing method for removing electromagnetic interference (EMI) noise in a photoacoustic sensor signal includes providing a first control signal to an optical switch connected to a light source to block or transmit the optical signal; generating a mixed signal that includes a photoacoustic signal and first EMI noise when the optical switch transmits the optical signal, and second EMI noise when the optical switch blocks the optical signal; and removing the EMI noise from the photoacoustic sensor signal based on the mixed signal and the second EMI noise to generate a photoacoustic signal.

In an embodiment, generating the mixed signal and the second EMI noise includes converting the photoacoustic sensor signal into a first digital signal; receiving a second control signal synchronized with the first control signal; and classifying the first digital signal into one of the mixed signal and the second EMI noise based on the second control signal.

In an embodiment, generating the mixed signal and the second EMI noise further includes providing a first clock signal to the light source to control the light source to modulate an intensity of the optical signal according to a specific frequency, and a second clock signal synchronized with the first clock signal to a lock-in amplifier; receiving, by the lock-in amplifier, the photoacoustic sensor signal from the photoacoustic sensor, and detecting a signal according to the specific frequency based on the second clock signal from the photoacoustic sensor signal; and converting the signal detected by the lock-in amplifier into the first digital signal.

In an embodiment, the method further includes analyzing the mixed signal and the second EMI noise to estimate information about the photoacoustic signal. Analyzing the mixed signal and the second EMI noise includes analyzing the second EMI noise to derive an x-component and a y-component of the second EMI noise; analyzing the mixed signal to derive an x-component and a y-component of the mixed signal; and estimating the information of the photoacoustic signal based on the x-component and the y-component of the second EMI noise and the x-component and the y-component of the mixed signal.

As is apparent from the above, in various sensor systems, EMI noise can be generated by sensor operation, signal processing circuits, and external devices, affecting the measurement signals, and resulting in errors in the measurement value. In sensor systems requiring high sensitivity and precision measurement, such as noninvasive biosignal measurement sensors and gas sensors, EMI noise can affect the measurement accuracy and reliability. Therefore, noise removal and compensation technologies are desirable for high-sensitivity sensing apparatuses. Embodiments of the present disclosure proposes a technology for measuring EMI noise and compensating a signal received from an analyte.

Through the disclosed technology, the performance of photoacoustic sensors and various sensing apparatuses including the photoacoustic sensors can be improved.

Through embodiments of the present disclosure, noninvasive blood glucose measurement technology can be commercialized by resolving the issues of low measurement accuracy in noninvasive blood glucose measurement technology. In addition, through the technology proposed by the present disclosure, the measurement accuracy and reliability of various existing sensing technologies, such as noninvasive biosignal sensors, gas sensors and the like, which require ultra-high-sensitivity measurement technology, can be improved.

The effects of the present disclosure are not limited to the effects described above, and other effects that are not described may be understood by those skilled in the art from the above detailed description.

Although specific embodiments of the present disclosure have been described in detail as descried above, those of ordinary skill in the technical field to which the present disclosure pertains should be able to understand that various modifications and alterations may be possible.

What is claimed is:

1. A photoacoustic sensing apparatus comprising:

a light source that directs an optical signal toward an analyte;

a photoacoustic sensor that receives an ultrasonic wave generated from the analyte and generates a photoacoustic sensor signal;

a signal processing device that controls the directing of the optical signal toward the analyte, and removes electromagnetic interference (EMI) noise from the photoacoustic sensor signal to generate a photoacoustic signal; and an optical switch that blocks or transmits the optical signal in response to a first control signal output from the signal processing device, wherein the signal processing device generates a mixed signal including the photoacoustic signal and first EMI noise when the optical switch transmits the optical signal, and generates second EMI noise when the optical switch blocks the optical signal, and wherein the signal processing device classifies the photoacoustic sensor signal into one of the mixed signal and the second EMI noise based on the first control signal, and analyzes the mixed signal and the second EMI noise to estimate information about the photoacoustic signal.

2. The photoacoustic sensing apparatus of claim 1, wherein:

the signal processing device generates a first clock signal and transmits the generated first clock signal to the light source; and the light source modulates an intensity of the optical signal according to a specific frequency determined by the first clock signal.

3. The photoacoustic sensing apparatus of claim 1, wherein the signal processing device includes:

a switch controller that generates the first control signal and a second control signal, and provides the first control signal to the optical switch to control the directing of the optical signal toward the analyte;

an analog-to-digital converter (ADC) that converts the photoacoustic sensor signal into a digital signal;

a selector that classifies the digital signal into one of the mixed signal and the second EMI noise based on the second control signal of the switch controller; and a processor that analyzes the mixed signal and the second EMI noise to estimate information about the photoacoustic signal.

4. The photoacoustic sensing apparatus of claim 3, wherein the second control signal is synchronized with the first control signal.

5. The photoacoustic sensing apparatus of claim 3, wherein the ADC outputs the mixed signal when the first control signal sets the optical switch to an ON state, and wherein the ADC outputs the second EMI noise when the first control signal sets the optical switch to an OFF state.

6. The photoacoustic sensing apparatus of claim 3, wherein the signal processing device further includes a signal generator that transmits a first clock signal to the light source such that the light source modulates an intensity of the optical signal according to a specific frequency.

7. The photoacoustic sensing apparatus of claim 6, wherein the signal processing device further includes a lock-in amplifier that receives the photoacoustic sensor signal from the photoacoustic sensor, receives a second clock signal synchronized with the first clock signal from the signal generator, and detects a signal according to the specific frequency based on the second clock signal from the photoacoustic sensor signal, and wherein the ADC converts the signal according to the specific frequency into the digital signal and then provides the digital signal to the selector.

8. The photoacoustic sensing apparatus of claim 3, wherein the information includes an amplitude and a phase of the photoacoustic signal.

9. The photoacoustic sensing apparatus of claim 3, wherein the processor detects the mixed signal and the second EMI noise by dividing each of the mixed signal and the second EMI noise into an x-component and a y-component, and estimates the information about the photoacoustic signal based on a difference between the x-components of the mixed signal and the second EMI noise and a difference between the y-components of the mixed signal and the second EMI noise.

10. A signal processing device for removing electromagnetic interference (EMI) noise in a photoacoustic sensor signal, wherein the photoacoustic sensor signal is generated by a photoacoustic sensor based on an ultrasonic wave signal generated from an analyte to which an optical signal is directed, the signal processing device comprising:

a switch controller that generates a first control signal and a second control signal, and provides the first control signal to an optical switch to control directing of the optical signal toward the analyte;

an analog-to-digital converter (ADC) that converts the photoacoustic sensor signal into a digital signal;

a selector that classifies the digital signal into one of a mixed signal and second EMI noise based on the second control signal of the switch controller, the mixed signal including a photoacoustic signal and first EMI noise; and a processor that analyzes the mixed signal and the second EMI noise to estimate information of the photoacoustic signal, wherein the switch controller synchronizes the second control signal with the first control signal, wherein the selector classifies the digital signal into the mixed signal based on the second control signal when the first control signal sets the optical switch to an ON state, and wherein the selector classifies the digital signal into the second EMI noise based on the second control signal when the first control signal sets the optical switch to an OFF state.

11. The signal processing device of claim 10, further comprising:

a signal generator that transmits a first clock signal to the light source such that the light source modulates an intensity of the optical signal according to a specific frequency; and a lock-in amplifier that receives the photoacoustic sensor signal from the photoacoustic sensor, receives a second clock signal synchronized with the first clock signal from the signal generator, and detects a signal according to the specific frequency based on the second clock signal from the photoacoustic sensor signal, wherein the ADC converts the signal according to the specific frequency into the digital signal and provides the digital signal to the selector.

12. The signal processing device of claim 10, wherein the processor detects the mixed signal and the second EMI noise by dividing each of the mixed signal and the second EMI noise into an x-component and a y-component, and estimates the information of the photoacoustic signal based on a difference between the x-components of the mixed signal and the second EMI noise and a difference between the y-components of the mixed signal and the second EMI noise.

13. A photoacoustic sensing method for removing electromagnetic interference (EMI) noise in a photoacoustic sensor signal, wherein the photoacoustic sensor signal is generated by a photoacoustic sensor based on an ultrasonic wave signal generated from an analyte to which an optical signal is directed, the photoacoustic sensing method comprising:

providing a first control signal to an optical switch connected to a light source to block or transmit the optical signal;

generating a mixed signal that includes a photoacoustic signal and first EMI noise based on the photoacoustic sensor signal when the optical switch transmits the optical signal, and second EMI noise based on the photoacoustic sensor signal when the optical switch blocks the optical signal; and removing the EMI noise from the photoacoustic sensor signal based on the mixed signal and the second EMI noise to generate a photoacoustic signal.

14. The method of claim 13, wherein generating the mixed signal and the second EMI noise includes:

converting the photoacoustic sensor signal into a first digital signal;

receiving a second control signal synchronized with the first control signal; and classifying the first digital signal into one of the mixed signal and the second EMI noise based on the second control signal.

15. The method of claim 14, wherein generating the mixed signal and the second EMI noise further includes:

providing a first clock signal to the light source to control the light source to modulate an intensity of the optical signal according to a specific frequency, and a second clock signal synchronized with the first clock signal to a lock-in amplifier;

receiving, by the lock-in amplifier, the photoacoustic sensor signal from the photoacoustic sensor, and detecting a signal according to the specific frequency based on the second clock signal from the photoacoustic sensor signal; and converting the signal detected by the lock-in amplifier into the first digital signal.

16. The method of claim 13, further comprising analyzing the mixed signal and the second EMI noise to estimate information about the photoacoustic signal, wherein analyzing the mixed signal and the second EMI noise includes:

analyzing the second EMI noise to derive an x-component and a y-component of the second EMI noise;

analyzing the mixed signal to derive an x-component and a y-component of the mixed signal; and estimating the information of the photoacoustic signal based on the x-component and the y-component of the second EMI noise and the x-component and the y-component of the mixed signal.

* * * * *